(12) United States Patent
Arstad et al.

(10) Patent No.: US 7,799,947 B2
(45) Date of Patent: Sep. 21, 2010

(54) IN VIVO IMAGING COMPOUNDS

(75) Inventors: Erik Arstad, London (GB); Gjermund Henriksen, Oslo (NO)

(73) Assignee: Hammersmith Imanet Limited, London (GB)

( * ) Notice: Subject to any disclaimer, the term of this patent is extended or adjusted under 35 U.S.C. 154(b) by 0 days.

(21) Appl. No.: 12/094,512

(22) PCT Filed: Nov. 28, 2006

(86) PCT No.: PCT/GB2006/004423

§ 371 (c)(1),
(2), (4) Date: Nov. 6, 2008

(87) PCT Pub. No.: WO2007/063286

PCT Pub. Date: Jun. 7, 2007

(65) Prior Publication Data

US 2009/0155168 A1    Jun. 18, 2009

Related U.S. Application Data

(60) Provisional application No. 60/740,464, filed on Nov. 29, 2005.

(51) Int. Cl.
C07C 257/18 (2006.01)
A61K 31/155 (2006.01)
A61K 51/00 (2006.01)
A61K 49/00 (2006.01)

(52) U.S. Cl. ............... 564/247; 514/637; 424/1.81; 424/1.85

(58) Field of Classification Search ............ None
See application file for complete search history.

(56) References Cited

U.S. PATENT DOCUMENTS

| | | | | |
|---|---|---|---|---|
| 4,252,951 | A * | 2/1981 | Jackson et al. | 540/220 |
| 6,291,499 | B1 * | 9/2001 | Thompson et al. | 514/387 |
| 6,362,196 | B1 * | 3/2002 | Kulagowski | 514/307 |

FOREIGN PATENT DOCUMENTS

| WO | 00/67751 | 11/2000 |
|---|---|---|
| WO | 01/30330 | 5/2001 |

OTHER PUBLICATIONS

Braga et al., Chem. Commun. (2005), 29, p. 3635-3645.*
Hamill, et.al., "The synthesis of a benzamidine-containing NR2B-selective NMDA receptor ligand labeled with tritium or fluorine-18" J. of Labelled Compounds andRadiopharmaceuticals, vol. 48, No. 1, Nov. 30, 2004, pp. 1-20.
Claiborne, et.al. "Orally efficacious NR2B-selective NMDA receptor antagonists" bioorganic & Medicinal Chemistry Letters, 13(4), 697-700, (2003).
Waterhouse, "Imaging the PCP site of the NMDA ion channel" Nuclear Medicine and Biology, Elsevier, NY, US, vol. 30, No. 8, Nov. 2003, pp. 869-878.
Arstad, et.al. "Towards NR2B receptor selective imaging agents for PET-synthesis and evaluation of N-[<11>C]-(2-methoxy)benzyl (E)-styrene-,2-naphthyl- and 4-trifluoromethoxyphenylamidine" Bioorganic & Medicinal Chemistry, Elsevier Science Ltd. vol. 14, No. 18 Sep. 15, 2006 pp. 6307-6313.
Jia, et.al. "1-(2-Naphthyl)-1H-pyrazole-5-carboxylamides as potent factor Xa inhibitors. Part 3: design, synthesis and SAR of orally bioavailable benzamidine-P4 inhibitors" Bioorganic & Medicinal Chemistry Letters 14 (2004) pp. 1229-1234.
Donkor, et.al. "Inhibitory effects of pentamidine analogues on spermine stimulated ligand binding to the NMDA receptor complex" Bioorganic & Medicinal Chemistry Letters. vol. 7 No. 11, pp. 14551460, 1997.
Zhang, et.al. "Design, synthesis and SAR of anthranilamide-based factor Xa inhibitors with improved functional activity" Biorganic & Medicinal Chemistry Letters 14 (2004) pp. 989-993.
PCT/GB2006/004423 Int'l Search Report/Written Opinion dated Nov. 2007.
Haradahira, e.tla. "In Vitro and In Vivo Evaluation of a C-11 Labeled Cinnamamide as a New Pet Radiogland for NR2B/NMDA Receptors" Proc. SNM 41st Annual Meeting, Jun. 2004, J. Nucl. Mes. No. 1376, pp. 441-442.

* cited by examiner

*Primary Examiner*—Brian J Davis

(57) ABSTRACT

The invention relates to a compound of formula (I) having use for in vivo imaging of the NR2B subtype of the NMDA receptor.

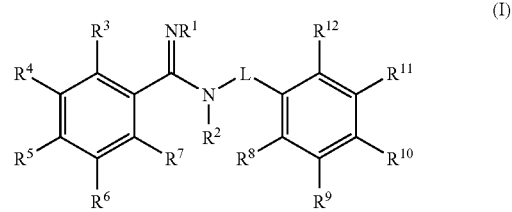

(I)

9 Claims, 4 Drawing Sheets

IN VIVO IMAGING COMPOUNDS

This application is a filing under 35 U.S.C. 371 of international application number PCT/GB2006/004423, filed Nov. 28, 2006, which claims priority to application No. 60/740,464 filed Nov. 29, 2005, in The United States the entire disclosure of which is hereby incorporated by reference.

The present invention relates to a class of amidine derivatives and their use for in vivo imaging using positron emission tomography (PET) or single photon emission computed tomography (SPECT). In particular, this invention relates to amidines which are selective antagonists for the NR2B subtype of the NMDA receptor and which carry a radiolabel ($^{123}$, $^{124}$, $^{122}$I, $^{11}$C, $^{18}$F) suitable for imaging with PET or SPECT. The compounds of the present invention are thus useful for in vivo imaging of the NR2B subtype of the NMDA receptor.

N-methyl-D-aspartate (NMDA) receptors are vital to a wide range of biological processes, including neuroprotection, neurodegeneration, long-term potentiation, memory and cognition (Yamada and Nabesima, 2003). They are among the most tightly regulated neurotransmitter receptors known, with six distinct binding sites for endogenous ligands influencing the probability of ion-channel opening. The defining feature of the NMDA receptor is that it allows calcium ions to flow into the postsynaptic neuron when glutamate is released into the synapse. This triggers a series of biochemical changes that result in modulation of postsynaptic currents. NMDA receptors consist of tetrameric heteromeric subunit-assemblies that have different physiological and pharmacological properties, and are differentially distributed throughout the Central Nervous System (CNS). Functional receptors in the mammalian CNS are formed by a combination of an NR1 and one or more of the four NR2 subunits (NR2A-D), which express the glycine and glutamate recognition sites, respectively. NR2A receptors are distributed ubiquitously in the CNS, with highest densities occurring in hippocampal regions, and NR2B is expressed predominantly in the forebrain but not in cerebellum, where NR2C predominates (Parsons et al., 1998). Expression of NR2D virtually complement to that of NR2A in being high in the midbrain and hindbrain but low in the forebrain. NMDA receptors are implicated in a wide range of pathological processes, including Alzheimer's disease, Parkinson's disease, Huntington's Chorea, epilepsy, schizophrenia, diabetes, anxiety, depression, chronic pain and drug abuse (Parsons et al., 1998; Loftis and Janowsky, 2003). A review of the properties and clinical implications of NR2B may be found in Loftis et al, Pharmacology & Therapeutics 97 (2003) 55-85.

WO 01/30330 describes certain NR2B [$^{125}$I]radioligands used for in vitro assay of therapeutic compounds.

WO 00/67751 describes amidine derivatives having use as NMDA NR2B antagonists for relieving, treating or preventing neurodegenerative diseases.

Hamill et al, J. Labelled Compounds and Radiopharmaceuticals, 2005, 48, 1-10 describes a benzamidine-containing NMDA NR2B receptor ligand labelled with tritium or fluorine-18.

However, there still exists a need for improved agents suitable for in vivo imaging of the NR2B receptor subtype of the NMDA receptor with good affinity for the receptor and favourable metabolic profile.

SUMMARY OF THE INVENTION

Figure 1:
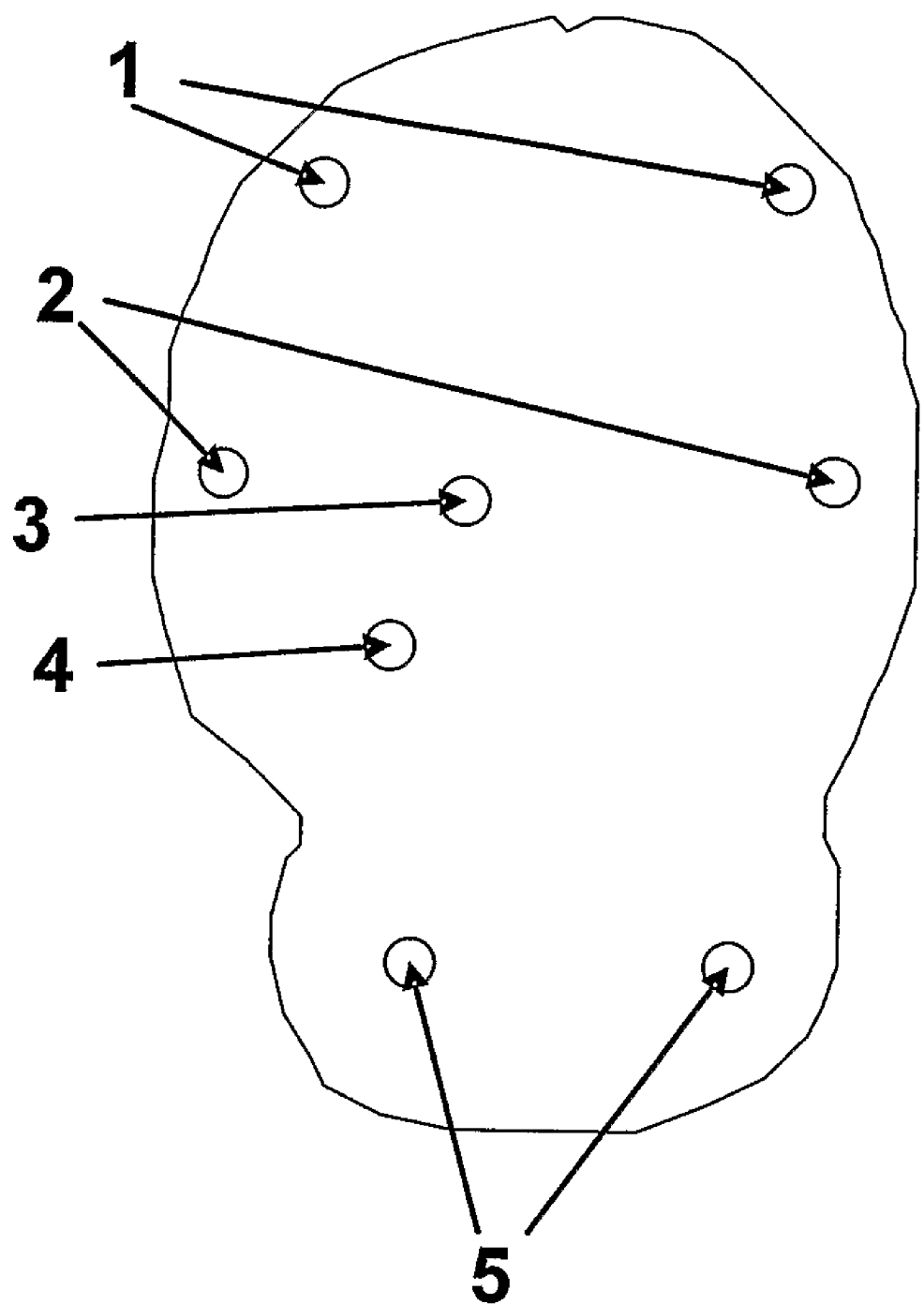
FIG. 1 illustrates the region of interest (ROI) selection on a transversal section, in which 1 is Frontal Cortex, 2 is Temporal Cortex, 3 is Thalamus, 4 is Hippocampal Formation, and 5 is Cerebellum.

The present invention provides a class of aryl amidine derivatives which are antagonists of the human NMDA receptor, being selective for those containing the NR2B subunit, and that carry a radionuclide suitable for PET or SPECT imaging. As such the compounds will be useful for imaging the NR2B receptor in the living human brain, and may therefore find use in diagnosis or therapy monitoring of diseases in which the NMDA receptor is implicated. The may also find use in the development of treatments for such diseases, in establishing dose levels required for efficient treatment or to establish if drugs intended to target the NR2B receptor successfully do so in the living human brain.

According to the invention, there is provided a compound of formula (I)

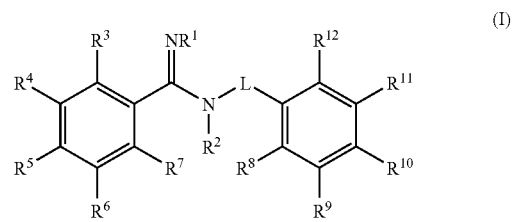

or a salt or solvate thereof, wherein:

$R^1$ is selected from hydrogen, $C_{1-6}$alkyl, $C_{2-6}$alkenyl, $C_{2-6}$alkynyl, $C_{5-12}$aryl, $C_{5-12}$hetaryl, and hydroxy;

$R^2$ is selected from hydrogen, $C_{1-6}$alkyl, $C_{2-6}$alkenyl, $C_{2-6}$alkynyl, $C_{5-12}$aryl, and $C_{5-12}$hetaryl;

L is $C_{1-6}$alkylene;

one or two of the groups $R^3$ to $R^7$ are independently selected from halo, $C_{1-6}$alkyl, $C_{1-6}$haloalkyl, $C_{1-6}$alkoxy, $C_{1-6}$haloalkoxy, phenyl, phenyl$C_{1-4}$-alkyl, and halophenyl$C_{1-4}$alkenyl, and the remaining groups $R^3$ to $R^7$ are hydrogen; one, two, three, or four of the groups $R^8$ to $R^{12}$ are independently selected from halo, $C_{1-6}$alkyl, $C_{1-6}$haloalkyl, $C_{1-6}$alkoxy, $C_{1-6}$haloalkoxy and the remaining groups $R^8$ to $R^{12}$ are hydrogen;

provided that (i) when $R^5$ is $C_{1-6}$alkoxy or $C_{1-6}$haloalkoxy and $R^3$, $R^4$, $R^6$, and $R^7$ are hydrogen two, three, or four of the groups $R^8$ to $R^{12}$ are independently selected from halo, $C_{1-6}$alkyl, $C_{1-6}$haloalkyl, $C_{1-6}$alkoxy, $C_{1-6}$haloalkoxy;

(ii) at least one of the groups $R^1$ to $R^{12}$ comprises a radiolabel selected from $^{11}$C, $^{18}$F, $^{123}$I, $^{124}$I, and $^{122}$I.

$R^1$ is suitably selected from hydrogen and $C_{1-6}$alkyl, more suitably hydrogen or methyl, and most suitably hydrogen.

$R^2$ is suitably selected from hydrogen and $C_{1-6}$alkyl, more suitably hydrogen or methyl, and most suitably hydrogen.

L is suitably methylene.

In groups $R^1$ to $R^{12}$, the radiolabel may be incorporated in the groups halo, $C_{1-6}$alkyl, $C_{1-6}$haloalkyl, $C_{1-6}$alkoxy, $C_{1-6}$haloalkoxy in the form:

-[$^{18}$F]fluoro;

-[$^{123, 124, 122}$I]iodo;

-[$^{11}$C]$C_{1-6}$alkyl such as -[$^{11}$C]methyl or -[$^{11}$C]CH$_2$—C$_{1-5}$alkyl, suitably -[$^{11}$C]methyl;

-[$^{11}$C]$C_{1-6}$alkoxy such as -[$^{11}$C]methoxy;

-[$^{11}$C]halo$C_{1-6}$alkyl such as -[$^{11}$C]halomethyl or -[$^{11}$C]CH$_2$—C$_{1-6}$haloalkyl;

-[$^{11}$C]halo$C_{1-6}$alkoxy such as -[$^{11}$C]halomethoxy;

-[$^{18}$F]$C_{1-6}$fluoroalkyl, such as -[$^{18}$F]fluoromethyl or -[$^{18}$F]trifluoromethyl;

-[$^{18}$F]$C_{1-6}$fluoroalkoxy, such as -[$^{18}$F]fluoromethoxy or -[$^{18}$F]trifluoromethoxy;

-[$^{123, 124, 122}$I]$C_{1-6}$iodoalkyl, such as -[$^{123, 124, 122}$I]iodomethyl;

-[$^{123, 124, 122}$I]$C_{1-6}$iodoalkoxy, such as -[$^{123, 124, 122}$I]iodomethoxy.

In one preferred substitution pattern, $R^5$ is selected from halo, $C_{1-6}$alkyl, $C_{1-6}$haloalkyl, $C_{1-6}$alkoxy, and $C_{1-6}$haloalkoxy and the remaining groups $R^3$ to $R^7$ are hydrogen, preferably in this aspect of the invention, $R^5$ is halo, suitably iodo, more suitably -[$^{123, 124, 122}$I]iodo.

In one aspect of the invention, when $R^5$ is iodo, it is suitably -[$^{123}$I]iodo or -[$^{124}$I]iodo.

According to a particular aspect of the invention, there is provided a compound of formula (Ia)

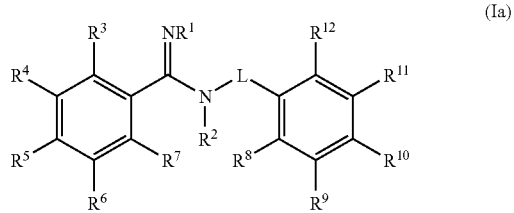

(Ia)

or a salt or solvate thereof, wherein $R^1$ is selected from hydrogen, $C_{1-6}$alkyl, $C_{2-6}$alkenyl, $C_{2-6}$alkynyl, $C_{5-12}$aryl, and $C_{5-12}$hetaryl;

$R^2$ is selected from hydrogen, $C_{1-6}$alkyl, $C_{2-6}$alkenyl, $C_{2-6}$alkynyl, $C_{5-12}$aryl, and $C_{5-12}$hetaryl;

L is $C_{1-6}$alkylene;

one or two of the groups $R^3$ to $R^7$ are independently selected from halo, $C_{1-6}$alkyl, $C_{1-6}$haloalkyl, $C_{1-6}$alkoxy, $C_{1-6}$haloalkoxy and the remaining groups $R^3$ to $R^7$ are hydrogen;

two, three, or four of the groups $R^8$ to $R^{12}$ are independently selected from halo, $C_{1-6}$alkyl, $C_{1-6}$haloalkyl, $C_{1-6}$alkoxy, $C_{1-6}$haloalkoxy and the remaining groups $R^8$ to $R^{12}$ are hydrogen and at least one of the groups $R^8$ to $R^{12}$ comprises a radiolabel selected from $^{11}$C, $^{18}$F, $^{123}$I, $^{124}$I, and $^{122}$I.

Compounds of formula (Ia) have surprisingly been found to have improved properties as in vivo imaging agents, for example having sufficient metabolic stability for in vivo imaging while retaining sufficient affinity.

Particular compounds of formula (I) comprising a radiolabel selected from $^{11}$C, $^{18}$F, $^{123}$I, $^{124}$I, and $^{122}$I include:

N-(3,5-dimethoxybenzyl)-4-trifluoromethoxyphenyl amidine;

N-(2,5-dimethoxybenzyl)-4-trifluoromethoxyphenyl amidine;

N-(2,6-dimethoxybenzyl)-4-trifluoromethoxyphenyl amidine;

N-(2,3-dimethoxybenzyl)-4-trifluoromethoxyphenyl amidine;

N-(2,5-dimethoxy-4-chlorobenzyl)-4-trifluoromethoxyphenyl amidine;

N-(2-methoxy-5-chlorobenzyl)-4-trifluoromethoxyphenyl amidine;

N-(2-methoxy-5-bromobenzyl)-4-trifluoromethoxyphenyl amidine;

N-(3-methoxy-5-chlorobenzyl)-4-trifluoromethoxyphenyl amidine;

N-(2-methoxybenzyl)-4-iodophenyl amidine;

N-(3-chlorobenzyl)-4-iodophenyl amidine;

N-(3,5-dichlorobenzyl)-4-iodophenyl amidine;

N-(3-(2-fluoroethoxy)-5-chlorobenzyl)-4-trifluoromethoxyphenyl amidine;

N-(3-(2-fluoroethoxy)-5-bromobenzyl)-4-trifluoromethoxyphenyl amidine; and

N-(2-(2-fluoroethoxy)-5-chlorobenzyl)-4-trifluoromethoxyphenyl amidine.

One preferred compound of formula (I), having favourable in vivo properties, is N-(2-[$^{11}$C]methoxy-5-bromobenzyl)-4-trifluoromethoxyphenyl amidine.

A further preferred compound of formula (I), having favourable in vivo properties, is N-(3-(2-[$^{18}$F]fluoroethoxy)-5-bromobenzyl)-4-trifluoromethoxyphenyl amidine.

Further preferred compounds of formula (I), having favourable in vivo properties, are N-(3-chlorobenzyl)-4-[$^{123, 124, 122}$I]iodophenyl amidine and N-(3,5-dichlorobenzyl)-4-[$^{123, 124, 122}$I]iodophenyl amidine.

Suitable salts of compounds of formula (I) or (Ia) include pharmaceutically acceptable salts formed from non-toxix acids or bases. Suitable acid salts include those formed with acetic, benzenesulphonic, citric, fumaric, glutamic, hydrobromic, hydrochloric, maleic, malic, methanesulphonic, succinic, sulphuric, tartaric, p-toluenesulphonic, phosphoric, or gluconic acid. Suitable basic salts include those formed with ammonium, calcium, magnesium, potassium, and sodium salts.

Suitable solvates of compounds of formula (I) or (Ia) include hydrates.

As mentioned above, the compounds of formula (I) and (Ia) are selective antagonists of the NR2B receptor subtype of the NMDA receptor and may therefore have utility for diagnostic purposes or therapy monitoring and to facilitate drug development of diseases in which the NMDA receptor is implicated.

By "diseases in which the NMDA receptor is implicated", is meant neurological and neurodegenerative disorders, including pain (in particular neuropathic pain and headache, specifically migraine), epilepsy, stroke, cerebral ischemia, muscular spasms, Alzheimer's disease, Huntington's disease, Parkinson's disease, schizophrenia, addiction (alcohol dependency and addiction to drugs of abuse), anxiety, depression, learning disorders, neurotoxicity associated with hypoxia and ischemia, and diabetes.

Therefore, according to a further aspect of the invention, there is provided a compound of formula (I) or (Ia) as defined above or a salt or solvate thereof, for use in medicine, suitably for in vivo imaging of the NMDA receptor in a mammal, preferably a human.

In the alternative, there is provided a method for in vivo imaging of NMDA receptor in a mammal, preferably a human, which comprises administration of an effective amount of a radiolabelled compound of formula (I) or a salt or solvate thereof and detecting the uptake of said compound.

Viewed from a further aspect the invention provides a method of monitoring the effect of treatment of a human or animal body with a drug to combat a disease in which the NMDA receptor is implicated, said method comprising administering to said body a compound of formula (I) or (Ia) or a salt or solvate thereof and detecting the uptake of said compound, said administration and detection optionally but preferably being effected repeatedly, e.g. before, during and after treatment with said drug.

The compounds of formula (I) or (Ia) may be used for in vivo imaging of the NMDA receptor in human and animal subjects and are therefore of use as research tools, for example, for the performance of competition studies which allow the interaction of a drug with the NMDA receptor to be studied. Such studies include dose-occupancy studies, determination of optimal therapeutic dose, drug candidate selection studies, determination of NMDA receptor distribution in the tissue of interest.

In use, the compounds of formula (I) or (Ia) may be administered alone, or preferably as a radiopharmaceutical formulation. A radiopharmaceutical formulation is defined as a formulation comprising a compound of formula (I) or (Ia) or a salt or solvate thereof and at least one pharmaceutically acceptable carrier or excipient, in a form suitable for administration to a mammal, preferably a human. Administration is suitably carried out by injection of the radiopharmaceutical formulation as an aqueous solution. The radiopharmaceutical formulations may further comprise further ingredients such as a buffer, pharmaceutically acceptable solubiliser (e.g. cyclodextrin or a surfactant such as Pluronic, Tween, or a phospholipid), pharmaceutically acceptable stabiliser or antioxidant (such as ascorbic acid, gentisic acid, or para-aminobenzoic acid). Such radiopharmaceutical formulations form a further aspect of the present invention.

The dose of a compound of formula (I) or (Ia) or a salt or solvate thereof will vary depending on the exact compound to be administered, the weight of the patient, the purpose of the imaging study and other variables as would be apparent to a physician skilled in the art. Generally, the dose of radiolabelled compound of formula (I) or (Ia) will lie in the range 0.01 to 100 mCi, preferably 0.1 to 50 mCi per 70 kg bodyweight. The dose administered needs to be such that a sufficient concentration of radioactivity accumulates in the tissue of interest to permit acquisition of good images between 30 and 320 minutes following administration of the compound of formula (I) or (Ia).

According to a further aspect of the invention, there is provided use of a compound of formula (I) or (Ia) or a salt or solvate thereof for the manufacture of a radiopharmaceutical for use in a method of in vivo imaging, suitably SPECT or PET, and preferably for imaging a disease in which the NMDA receptor is implicated; involving administration of said radiopharmaceutical to a human or animal body and generation of an image of at least part of said body.

The compounds of formula (I) and (Ia) and salts and solvates thereof may be prepared by conventional methods of organic chemistry and radiochemistry such as those described in WO 01/30330, WO 00/67751, and Hamill et al, J. Labelled Compounds and Radiopharmaceuticals, 2005, 48, 1-10. Further suitable methodologies are set out below and in the examples.

[$^{11}$C]methyl iodide may used to effect [$^{11}$C]methylation of a hydroxy-containing precursor. [$^{11}$C]methylation may be carried out in solution phase, dissolving the appropriate precursor in a solvent such as dimethylsulphoxide, dimethylformamide, acetonitrile, or acetone, and in the presence of a base, for example potassium carbonate, sodium hydroxide, or sodium hydride.

$^{18}$F is typically incorporated into a molecule either by nucleophilic or electrophilic fluorination methods. The fluorine may be incorporated directly, for example, by nucleophilic displacement of a leaving group by [$^{18}$F]fluoride, or by way of a $^{18}$F-fluorinated labelling agent which is prepared and then attached to the target molecule by a second reaction, such as an alkylation.

[$^{18}$F]fluoride is conveniently prepared from $^{18}$O-enriched water using the (p,n)-nuclear reaction, (Guillaume et al, Appl. Radiat. Isot. 42 (1991) 749-762) and generally isolated as the potassium salt which is dried and solubilised with a phase transfer agent such as a tetraalkylammonium salt or an aminopolyether (for example, Kryptofix 2.2.2). Nucleophilic displacement of a leaving group, often a sulphonic ester, such as triflate, nosylate, tosylate, or mesylate or a halo group such as iodo or bromo, may typically be effected by heating for 10 to 30 minutes at elevated temperatures, for example 80 to 160° C. in a polar aprotic solvent such as acetonitrile, dimethylsulphoxide, or dimethylformamide. Aromatic nucleophilic [$^{18}$F] fluorination may involve displacement of a nitro or tetraalkylammonium group.

Useful [$^{18}$F]labelling agents include the [$^{18}$F]fluoroalkylhalides, such as [$^{18}$F]fluoromethylbromide. These are routinely prepared by nucleophilic displacement of a suitable leaving group by [$^{18}$F]fluoride before being coupled to a suitable precursor.

$^{123, 124, 122}$I is commonly introduced to an organic molecule by electrophilic iodination of a trialkyltin precursor, such as a tributylstannyl compound, in the presence of an oxidising agent such as peracetic acid, N-chlorosuccinimide, and N-chlorotolylsulphonamide (for example chloramine-T or iodogen), at non-extreme temperature and in a suitable solvent such as an aqueous buffer. Radiohalogenation methods are reviewed in detail in Bolton, J Label. Compd Radiopharm 2002, 45, 485-528.

Hydroxyl-containing precursors of a compound of formula (I) or (Ia) which are suitable for [$^{11}$C]alkylation or [$^{18}$F] fluoroalkylation and [$^{127}$I]iodo precursors or trialkyl tin precursors which are suitable for conversion to [$^{123, 124, 122}$I]iodo compounds of formula (I) as described above may be prepared according to Scheme 1 wherein L and $R^1$ to $R^{12}$ are as defined for formula (I) or are precursors to such substituents as described in more detail above and in the examples.

Scheme 1

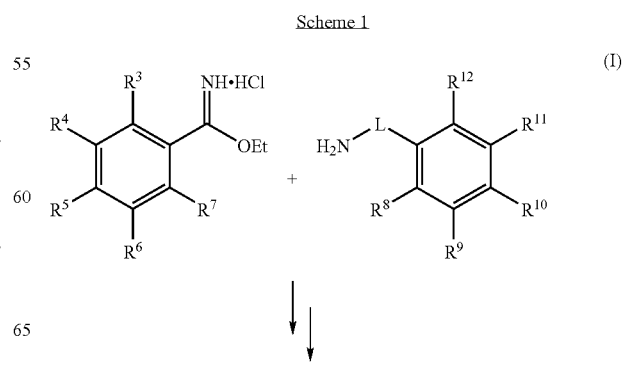

-continued

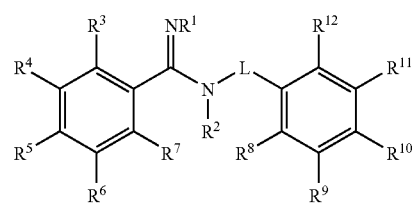

Certain precursors for the compounds of formula (I) and (Ia) which are useful as intermediates for radiolabelling are novel and therefore form a further aspect of the invention.

Thus, there is provided a compound of formula (IIa):

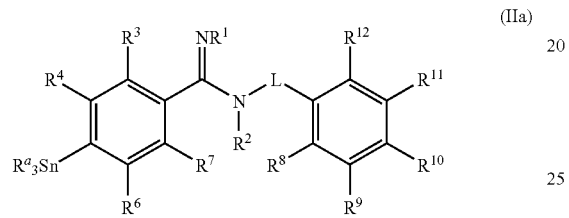

(IIa)

wherein each $R^a$ is selected from $C_{1-6}$alkyl and L and $R^1$ to $R^{12}$ are as defined above for the compounds of formula (I) or (Ia). In this aspect of the invention, $R^1$ to $R^7$ are preferably hydrogen, L is suitably methylene, $R^8$, $R^{10}$, and $R^{12}$ are preferably hydrogen, $R^9$ is preferably hydrogen or chloro, and $R^{11}$ is preferably chloro.

Useful hydroxyl-containing precursors of a compound of formula (I) or (Ia) which are suitable for [$^{11}$C]alkylation or [$^{18}$F]fluoroalkylation include a compound of formula (IIb):

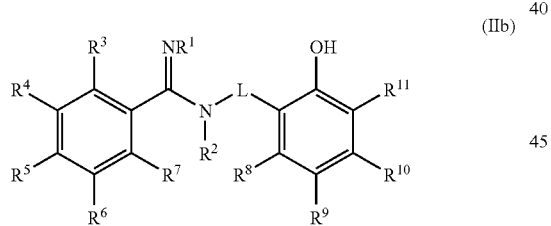

(IIb)

wherein L and $R^1$ to $R^{12}$ are as defined above for the compounds of formula (I) or (Ia). In this aspect of the invention, $R^1$ to $R^4$, $R^6$, $R^7$, $R^8$, $R^{10}$, $R^{11}$ are preferably hydrogen, $R^5$ is preferably $C_{1-6}$alkoxy or $C_{1-6}$haloalkoxy, most preferably trifluoromethoxy, and $R^9$ is preferably bromo or chloro.

The invention will now be illustrated by way of examples in which the following abbreviations are used:

THF: tetrahydrofuran min(s): minute(s)

h: hour(s)

DMF: N,N'-dimethylformamide

DCM: dichloromethane

DMSO: dimethylsulphoxide

Synthetic Examples

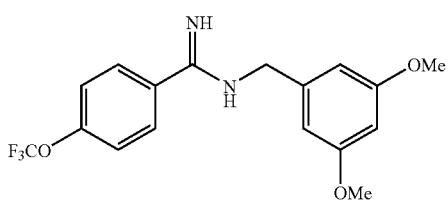
EA4

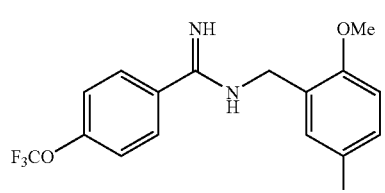
EA5

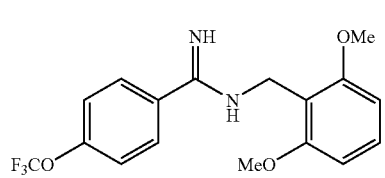
EA6

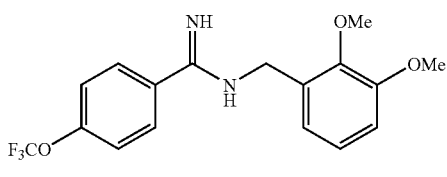
EA7

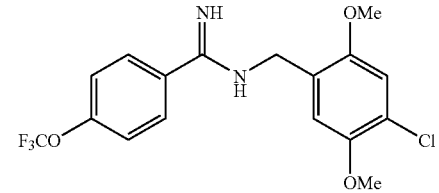
EA8

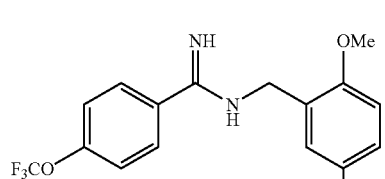
EA9

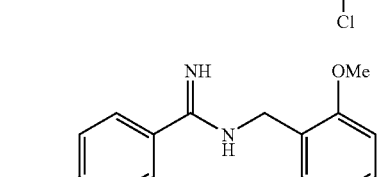
EA10

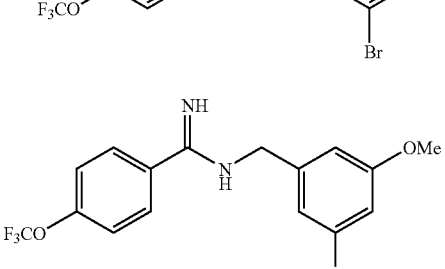
EA11

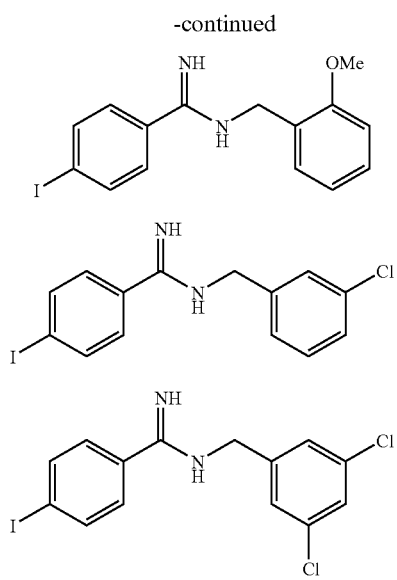
EA12
EA13
EA14
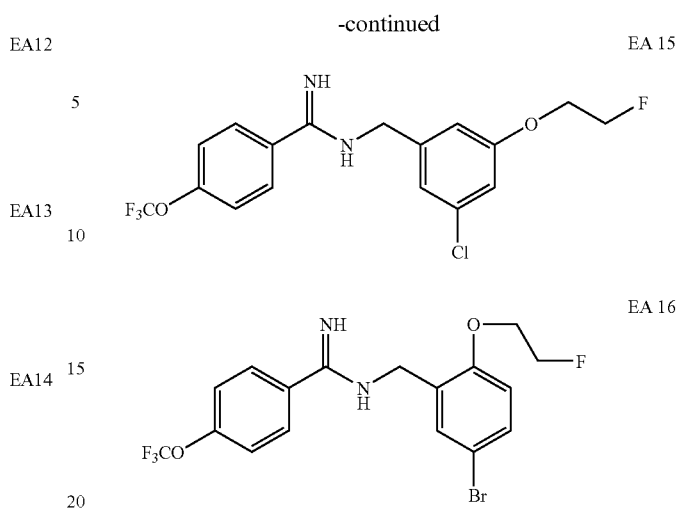
EA15
EA16
Compounds EA4-16 as set forth above may be prepared according to the following Scheme 2:
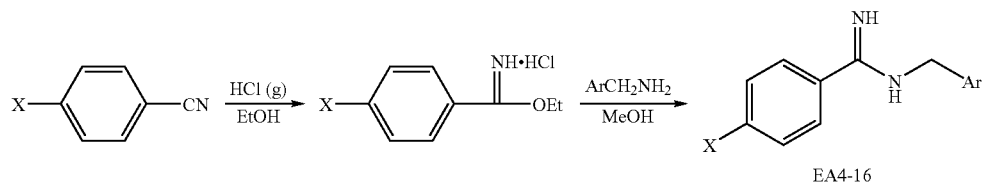
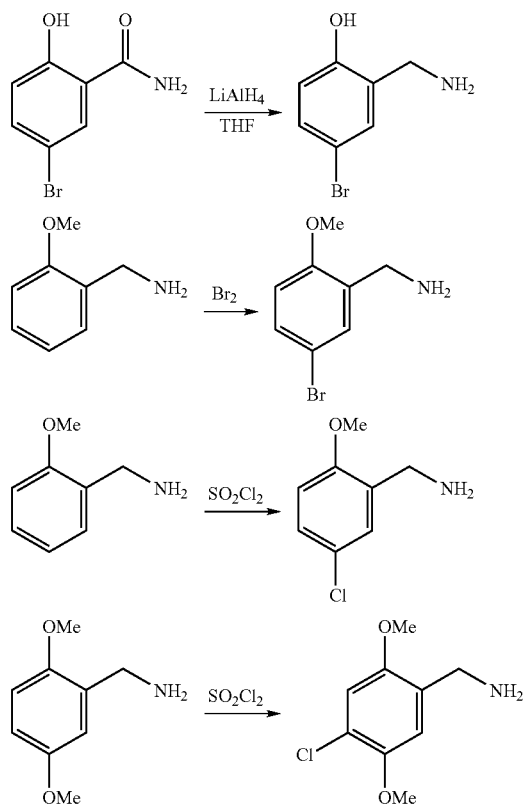

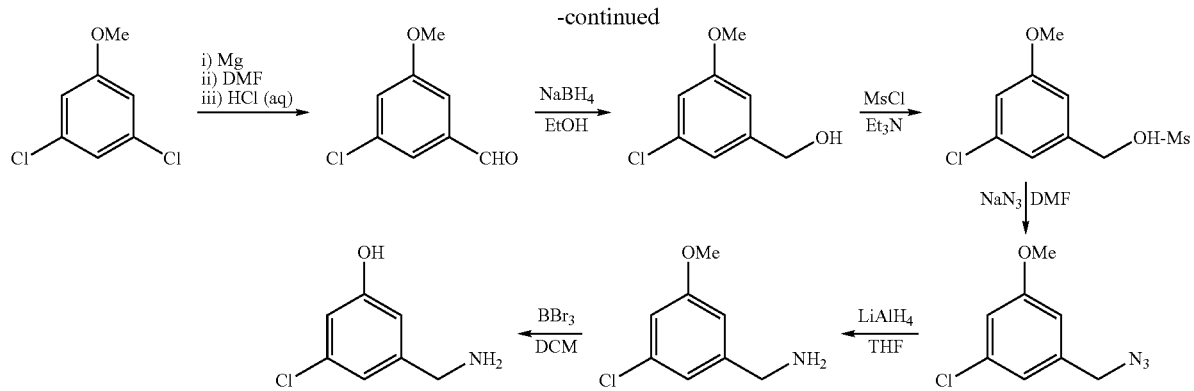

Scheme 2

EXPERIMENTAL

General Methods

Herein is reported the syntheses of compounds EA4 to EA16, including all intermediates. The reported chemical yields were not optimized. 4-trifluoromethoxybenzonitrile, 4-iodobenzonitrile, 3,5-dimethoxybenzylamine, 2,5-dimethoxybenzylamine and 2,3-dimethoxybenzylamine were obtained from Aldrich. All commercial reagents and solvents were used without further purification unless otherwise specified.

$^1$H NMR spectra were recorded on a JEOL ECP 500 (500 MHz) spectrometer or a AMX-300 (300 MHz) spectrometer using the solvent signal as an internal standard. The chemical shifts are reported in ppm downfield from zero, and coupling constants are reported in hertz (Hz). Column chromatography was performed on a CombiFlash Companion (ISCO, Inc.) using RediSep normal phase disposable flash columns (Kieselgel).

Intermediate 1

Step (a) 3-Chloro-5-methoxybenzaldehyde

To a mixture of dichloroanisole (60 mmol, 10.62 g), Mg (66 mmol, 1.60 g) and THF (30 ml) was added 1,2-dibromoethane (6 mmol, 1.13 g). The mixture was stirred until bubbles of gas started to evolve (2-3 min), and then heated to reflux for 2.5 h. The resulting dark brown mixture was cooled to −10° C. on an acetone-ice bath and DMF (90 mmol, 7 ml) was added slowly. After 20 min the ice-bath was removed, the mixture was stirred for 3 h and subsequently quenched with NH$_4$Cl (10% w/w in water, 100 ml). The product mixture was extracted with DCM (4×50 ml), the organic phase washed with water, then brine and dried (MgSO$_4$). Filtration and evaporation under reduced pressure gave a red liquid residue, which was purified by means of flash chromatography (silica, pentane/ether gradient. 5-30%) to provide the title compound (4.60 g, 45%) as a clear liquid. $^1$H NMR (DMSO, 300 MHz) δ 3.84 (s, 3H), 7.16 (s, 1H), 7.25 (s, 1H), 7.43 (s, 1H) and 9.92 (s, 1H).

Intermediate 1

Step (b) 3-Chloro-5-methoxybenzyl alcohol

To an ice-cold solution of 3-chloro-5-methoxybenzaldehyde (27 mmol, 4.60 g) in ethanol (90 ml) was added NaBH$_4$ (30 mmol, 1.14 g) in one portion under stirring. After 0.5 h the mixture was allowed to reach room temperature and stirred for another 0.5 h. HCl (2 M, ~25 ml)) was added slowly until no more hydrogen gas evolved, the resulting mixture was concentrated under reduced pressure and the residue separated between water and ether, the organic phase was washed with braine and dried (MgSO$_4$). Filtration and evaporation of solvents afforded the title compound (4.53 g, 97%) as a white solid. The product was used without further purification in the next step. An analytically pure sample was obtained be means of flash chromatography (silica, hexane/ether grad.). $^1$H NMR (CDCl$_3$, 500 MHz) δ 2.77 (br, 1H), 3.76 (s, 3H), 4.55 (s, 2H), 6.74 (s, 1H), 6.77 (s, 1H) and 6.88 (s, 1H).

Intermediate 1

Step (c) Methanesulfonic acid 3-Chloro-5-methoxybenzyl ester

To a solution of 3-chloro-5-methoxybenzyl alcohol (14.7 mmol, 2.54 g) in DCM (20 ml) was added Et$_3$N (22 mmol, 2.23 g, 3.1 ml) and the solution was cooled to −10° C. on an acetone-ice batch. Methanesulfonic chloride (17.7 mmol, 2.03 g, 1.4 ml) was added dropwise under stirring. After 45 min the mixture was separated between DCM and H$_3$PO$_4$ (5% v/v in water, cold). The organic phase was washed with H$_3$PO$_4$ (5% v/v in water, cold), NaHCO$_3$ (10% in water, cold), brine and dried (MgSO$_4$). Filtration and removal of solvents under reduced pressure yielded the title compound (3.43 g, 93%) as a white solid. The product was used in the next step without further purification. $^1$H NMR (CDCl$_3$, 500 MHz) δ 2.97 (s, 3H), 3.82 (s, 3H), 5.16 (s, 2H), 6.82 (s, 1H), 6.90 (s, 1H) and 6.98 (s, 1H).

Intermediate 1

Step (d) 3-Chloro-5-methoxybenzylazide

To a solution of methanesulfonic acid 3-chloro-5-methoxybenzyl ester (20 mmol, 5.01 g) in DMF (30 ml) was added NaN$_3$ (60 mmol, 3.90 g). The mixture was stirred for 3 h and the contents subsequently separated between water (300 ml) and DCM (150 ml). The organic phase was washed with water (2×100 ml), then brine, and dried (MgSO$_4$). Filtration and removal of solvents under reduced pressure yielded a yellow liquid (4.14 g). Purification by means of flash chromatography (silica, hexane/ether gradient 0-50%) provided the title compound (3.65 g, 93%). $^1$H NMR (CDCl$_3$, 500 MHz) δ 3.80 (s, 3H), 4.27 (s, 2H), 6.73 (s, 1H), 6.85 (s, 1H) and 6.89 (s, 1H).

Intermediate 1

3-Chloro-5-methoxybenzylamine

A solution of 3-chloro-5-methoxybenzylazide (5 mmol, 0.988 g) in THF (20 ml) was cooled to −78° C. and LiAlH$_4$ (1 M, 7.5 mmol, 7.5 ml) was added dropwise with stirring. After 30 min the reaction was allowed to reach 0° C. and the mixture was stirred for another 1 h. To the resulting sharp yellow solution was added ethyl acetate (0.3 ml), followed by water (0.3 ml), NaOH (15% w/w in water) and water (0.9 ml). The resulting mixture was filtered and the solids washed with acetonitrile (15 ml). The solvents were evaporated off to provide the title compound (0.792 g, 92%) as a clear, colorless liquid. The product was used in the next step without further purification. An analytical pure sample was obtained by means of flash chromatography (silica, DCM/MeOH/NH$_3$ (30%) 97/3/0.3 v/v/v). $^1$H NMR (CDCl$_3$, 500 MHz) δ 1.46 (br, 2H), 3.77 (s, 3H), 3.79 (s, 2H), 6.74 (s, 1H), 6.75 (S, 1H) and 6.87 (s, 1H).

Intermediate 2

4-Chloro-2,5-dimethoxybenzylamine hydrochloride

To 2,5-dimethoxybenzylamine (10 mmol, 1.678 g) was added ether (2 ml) and acetic acid (glacial, 18 ml). The resulting mixture was cooled on an ice-batch and SO$_2$Cl$_2$ (1.2 mmol, 1.62 g, 0.96 ml) was added dropwise with vigorous stirring. After 15 min the ice-bath was removed and the mixture was stirred for 1 h. Ether (20 ml) was added, the solids were filtered off and washed with a small amount of ether to give the title compound (1.16 g, 57%) as a cream colored solid. $^1$H NMR (DMSO, 300 MHz) δ 3.79 (s, 3H), 3.81 (s, 3H), 3.93 (s, 2H), 7.16 (s, 1H), 7.41 (s, 1H) and 8.48 (br, 3H).

Intermediate 3

5-Chloro-2-methoxybenzylamine hydrochloride

To acetic acid (glacial, 8 ml) was slowly added a solution of 2-methoxybenzylamine (40 mmol, 5.48 g) in ether (8 ml) under vigorous stirring. The resulting solution was cooled on an ice-bath and SO$_2$Cl$_2$ (50 mmol, 4.0 ml) was added dropwise. After 15 min the ice-bath was removed and the reaction was stirred for 3 h to give a white suspension. Ether (40 ml) was added, the mixture was stirred for 2 h, the solids were filtered off and washed with small amounts of ether to give a cream colored solid (6.29 g). The crude product was crystallized in ethanol/ether to give the title compound (2.48 g, 30%) as white crystals. $^1$H NMR (DMSO, 300 MHz) δ 3.82 (s, 3H), 3.92 (s, 2H), 7.19 (d, 1H), 7.43 (m, 2H) and 8.50 (br, 3H).

Intermediate 4

5-Bromo-2-methoxybenzylamine hydrobromide

To 2-methoxybenzylamine (30 mmol, 4.12 g) was added ether (6 ml) and acetic acid (glacial, 10 ml). The resulting solution was cooled on an ice-batch and Br$_2$ (30 mmol, 4.79 g, 1.54 ml) was added dropwise. After 1 h the ice-bath was removed and the mixture was stirred for another 1 h before addition of ether (20 ml). The resulting mixture was left in the cold for 0.5 h, the solids were filtered off and washed with ether (20 ml) to give a cream colored solid (6.29 g). The crude product was crystallized in ethanol/ether to give the title compound (4.62 g, 52%) as white crystalline material. $^1$H NMR (DMSO, 500 MHz) δ 3.84 (s, 3H), 3.98 (s, 2H), 7.05 (s, 1H), 7.58 (m, 2H) and 8.16. (br, 3H).

Intermediate 5

Ethyl 4-trifluoromethoxyphenyl imidate hydrochloride

This intermediate was prepared from 4-trifluoromethoxy-benzonitrile by methods analogous to those described in Claiborne, C. F et al Orally efficacious NR2B-selective NMDA receptor antagonists. *Bioorg. Med. Chem. Lett.* 2003, 13, 697-700.

General Method for Synthesis of EA4-11 Hydrochlorides

To a solution of ethyl 4-trifluoromethoxyphenyl imidate hydrochloride (1.0 mmol) in methanol (anhydrous, 2 mL) was added the appropriate amine intermediate (2.0 mmol). The mixture was stirred over night, solvents were evaporated off and the residue purified by crystallization in a solvent mixture of either acetone/ether or ethanol/ether. EA 4: $^1$H NMR (DMSO, 300 MHz) δ 3.74 (s, 6H), 4.89 (s, 2H), 6.50 (s, 1H), 6.65 (s, 2H), 7.61 (d, 2H), 7.97 (d, 2H), 9.61 (br, 1H), 9.83 (br, 1H) and 10.65 (br, 1H); EA 5: $^1$H NMR (DMSO, 300 MHz) δ 3.70 (s, 3H), 3.78 (s, 3H), 4.61 (s, 2H), 6.97 (m, 3H), 7.61 (d, 2H), 7.93 (d, 2H) and, 9.86 (m, br, 3H); EA 6: $^1$H NMR (DMSO, 300 MHz) δ 3.81 (s, 6H), 4.55 (s, 2H), 6.73 (d, 2H), 7.35 (t, 1H), 7.56 (d, 2H), 7.81 (d, 2H) and 9.71 (br, 3H); EA 7: $^1$H NMR (DMSO, 300 MHz) δ 3.80 (s, 3H), 3.82 (s, 3H), 4.85 (s, 2H), 6.95 (m, 1H), 7.08 (m, 2H), 7.60 (d, 2H), 7.97 (d, 2H) and 9.98 (br, 3H); EA 8: $^1$H NMR (DMSO, 500 MHz) δ 3.82 (s, 3H), 4.63 (s, 2H), 7.19 (s, 1H), 7.33 (s, 1H), 7.62 (d, 2H), 7.90 (d, 2H) and 9.81 (br, 1H); EA 9: $^1$H NMR (DMSO, 500 MHz) δ 3.88 (s, 3H), 4.66 (s, 2H), 7.10 (d, 1H), 7.40 (m, 2H), 7.62 (d, 2H), 7.94 (d, 2H), 9.52 (br, 1H), 9.86 (br, 1H) and 10.26 (br, 1H); EA 10: $^1$H NMR (DMSO, 300 MHz) δ 3.83 (s, 3H), 4.62 (s, 2H), 7.05 (d, 1H), 7.52 (m, 2H), 7.61 (d, 2H), 7.92 (d, 2H) and 9.87 (br, 2H); EA 11: $^1$H NMR (DMSO, 500 MHz) δ 3.79 (s, 3H), 4.71 (s, 2H), 7.00 (s, 1H), 7.12 (s, 1H), 7.18 (s, 1H), 7.62 (d, 2H), 7.98 (d, 2H) and 9.98 (br, 1H).

Intermediate 6

Ethyl 4-iodophenyl imidate hydrochloride

To p-iodobenzonitrile (10 mmol, 2.19 g) was added ethanol (25 mmol, 1.43 ml) and DCM (10 ml) under a protective atmosphere of nitrogen. The resulting solution was cooled on an acetone-ice batch to −5° C. to −10° C. and HCl gas was bubbled through the solution for 15 min. The resulting mixture was left in the cold for 3 weeks. The solvents were evaporated of, the resulting solid was suspended in ether (10 ml) and the mixture was sonificated for 5 min. The mixture was filtered, the solid washed with ether and dried to give the title compound as a cream colored solid (2.77 g, 89%).

General method for synthesis of EA12-14 Hydrochlorides

To a solution of the appropriate amine intermediate (4 mmol) in methanol (6 ml) was added ethyl 4-iodophenyl imidate hydrochloride (2 mmol). The reaction mixture was stirred over night, solvents evaporated off and the residue purified by crystallization in a mixture of ethanol and ether. EA12 was obtained in 36% yield,
EA13 in 68% yield and EA 14 in 60% yield. All compounds were obtained as cream colored solids.

EA 12: $^1$H NMR (DMSO, 300 MHz) δ 3.83 (s, 3H), 4.62 (s, 2H), 6.93-7.36 (m, 4H), 7.59 (d, 2H), 7.96 (d, 2H) and 9.85 (br, N—H); EA 13: $^1$H NMR (DMSO, 300 MHz) δ 4.77 (s, 2H), 7.35-7.64 (m, 6H), 7.96 (m, 2H) and 10.00 (br, N—H); EA 14: $^1$H NMR (DMSO, 300 MHz) δ 4.74 (s, 2H), 7.61 (m, 5H), 7.89 (m, 2H) and 9.91 (br, N—H)

Synthesis of Radioiodoinated EA12 to EA14

EA12 to EA14, radiolabelled with $^{124, 122, 123}$I may be prepared from the corresponding $^{127}$I compound, by conversion to a trialkyl tin, suitably trimethyl tin, analogue, and subsequently to the $^{124, 122, 123}$I compound using methods analogous to those described in Owens, J et al. Nuclear Medicine and Biology, vol 27, pp 557-564, 2000.

Intermediate 7

3-Chloro-5-hydroxy-benzylamine

A solution of 3-chloro-5-methoxybenzylamine (4.6 mmol, 0.792 g) in DCM (anhydrous, 20 ml) was cooled to −78° C. and BBr$_3$ (1 M in DCM, 9.43 mmol) was added dropwise. The reaction was allowed to reach room temperature over night with stirring. The reaction was quenched by careful addition of methanol (5 ml), solvents were evaporated under reduced pressure and the residue was purified by means of chromatography (silica, DCM/MeOH/NH$_3$ (30% in water) Sep. 1, 2001 v/v/v) to provide the title compound (0.48 g, 66%) as a white solid. (DMSO, 500 MHz) δ 3.61 (s, 2H), 4.57 (br, 1H), 6.62 (s, 1H), 6.80 (s, 1H) and 6.83 (s, 1H).

Intermediate 8

5-Bromo-2-hydroxy-benzylamine

To a suspension of LiAlH$_4$ (52.6 mmol, 2.0 g) in THF (40 ml) was added a solution of 5-Bromo-2-hydroxy-benzamide (20 mmol, 4.32 g) in THF (40 ml) and the resulting mixture was heated to reflux for 18 h. The mixture was cooled on an ice-bath and the reaction was quenched by careful addition of water (4 ml) followed by NaOH (50% w/w in water, 4 ml). The mixture was heated shortly to reflux at which point a white solid precipitated. The solids were filtered off, and the resulting yellow solution was acidified with HCl (1 M) until no more precipitates were formed (~15 ml HCl, pH~9). Filtration provided a mixture of the title compounds and 2-hydroxy-benzylamine (2.69 g) as a cream colored solid. Purification by means of chromatography (silica, DCM/(MeOH/NH$_3$ (30% in water) 10/1 v/v) grad.) provided the title compound (1.16 g, 27%) as a white solid. $^1$H NMR (DMSO, 500 MHz) δ 3.79 (s, 2H), 5.30 (br, 3H), 6.65 (d, 1H), 7.19 (d, 1H) and 7.27 (s, 1H)

General Procedure for Phenol Amidine Intermediates (Precursors for EA15 and EA16)

To a mixture of hydroxybenzylamine (0.9 mmol), NaOMe (1.1 mmol) and MeOH (anhydr. 10 ml) was added ethyl 4-trifluoromethoxyphenyl imidate hydrochloride (1.0 mmol). The reaction mixture was stirred over night and quenched with HCl (0.5 ml conc. in 5 ml MeOH). The resulting mixture was concentrated under reduced pressure and the residue purified by means of chromatography (silica, DCM/(MeOH/NH$_3$ (30% in water) 10/1 v/v) grad.) 8.5/1.35/0.15 v/v/v). Precursor for EA 15: $^1$H NMR (DMSO, 500 MHz) δ 4.25 (s, 2H), 6.63 (s, 1H), 6.83 (s, 1H), 6.87 (s, 1H), 7.39 (d, 2H) and 7.96 (d, 2H); Precursor for EA16: $^1$H NMR (DMSO, 500 MHz) δ 3.79 (s, 1H), 4.32 (s, 2H), 6.65 (d, 1H), 7.24 (m, 2H), 7.46 (d, 2H) and 7.82 (d, 2H).

General Procedure for Synthesis of EA15 and EA16

To the phenol amidine (0.24 mmol) was added 4-methylphenylsulfonic acid 1-fluoroethyl ester (0.24 mmol), K$_2$CO$_3$ (4.8 mmol) and acetone (6 ml). The resulting mixture was heated to reflux for 3 days. The mixture was filtered and solvents evaporated off. The residue was purified by means of chromatography (silica, ethyl acetate/Et$_3$N 97/3 v/v). Traces of Et$_3$N was removed from the product by adding NH3 (30% in water) and concentrating under reduced pressure. EA 15: $^1$H NMR (CDCl$_3$, 500 MHz) δ 4.31 (dd, 2H), 4.78 (overlap dd, 2H and s, 2H), 7.08 (s, 1H), 7.17 (s, 1H), 7.19 (s, 1H), 7.63 (d, 2H), 7.98 (d, 2H), 9.68 (br, 1H), 9.86 (br, 1H) and 10.70 (br, 1H); EA 16: $^1$H NMR (CDCl$_3$, 500 MHz) δ 4.25 (dd, 2H), 4.53 (s, 2H), 4.76 (dd, 2H) 6.75 (d, 1H) and 7.46 (m, 6H).

General procedure for synthesis of N-(3-chlorobenzyl)-4-trialkyltinphenyl amidine; N-(3,5-dichlorobenzyl)-4-trialkyltinphenyl amidine The title intermediates may be prepared by the methods described in US patent application US2003/001838 A1.

$^{11}$C-Labelling of Compound EA11

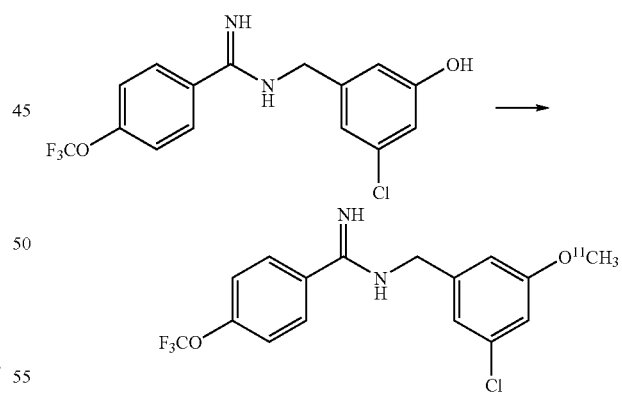

Method 1

$^{11}$C-MeI was prepared using the classic "wet" method. Beam current: 5 μA for 1 minute (0.08 μAhr) Expected starting activity of $^{11}$C02: 25mCi (150 mCi from 1 min 30 μA)

Synthesis time: 41 mins $^{11}$C-MeI was distilled into a solution of precursor (1.05 mg) powdered sodium hydroxide (1.87 mg) and anhydrous DMF (200 μl). The suspension was heated with magnetic stirring for 5 minutes at 50° C.

The crude reaction mixture was diluted with water (5 ml) then passed through a short column of reverse phase HPLC packing material to partially purify the reaction mixture. The material trapped on this column was then eluted off onto a semi-preparative HPLC column (Phenomenex Ultracarb 7 ODS 30) eluent: 45 $CH_3CN$/55 0.05 molar sodium dihydrogen orthophosphate at 3 ml/min. The eluent from the column was monitored for UV absorption at 240 nm and for radioactivity.

Product peak was collected and analysed by reverse phase HPLC (see Kawai results)

Results

Product radioactivity: 1.06 mCi decay corrected yield from C02: 17%

Retention time of product peak: 16.4 mins

Retention time of precursor: 5 mins approx.

Method 2 ($^{11}$C Labelled EA10 and EA11)

10 µmol of des-methyl compound in question was dissolved in 0.25 ml of anhydrous N,N-dimethyl formamide and added to a septum-sealed vial containing 50 µmol of sodium hydride. The vial was flushed with and maintained under argon gas. [$^{11}$C]$CH_3$I, prepared from cyclotron produced [$^{11}$C]$CO_2$ by the catalytic gas-phase iodination reaction via [$^{11}$C]$CH_4$ (GE MeI MicroLab), was led into the vial kept at −20° C. After trapping of the alkylation agent, the reaction mixture was heated at 80° C. for 5 min. For purification, the reaction mixture was diluted with 1 ml of a solution consisting of MeCN:0.1 M ammonium formate (30:70 V/V), loaded into a 2 ml injection loop and transferred onto a semi-preparative column (ID: 8 mm; length: 300 mm; µ-Bondapak CS-Chromatograhphie Service) eluted with MeCN:0.1 M ammonium formate (48:52 V/V). The eluent from the column was continuously monitoring for radioactivity (BioScan PIN-detector) and UV absorbance (254 nm).

For animal experiments, the fraction containing the product was diluted 1:2 with water and applied to a RP18 Sep-Pak Plus cartridge (Waters), which had in advance been preconditioned with 10 ml of MeCN followed by 10 ml of water. After product fixation, the cartridge was washed with 10 ml of water. The product eluted with diethyl ether. After evaporation of the ether, the residue was dissolved in phosphate buffered saline (pH 7.4).

$^{11}$C-labelled analogues of EA4 to EA12 may be prepared by analogous methods.

$^{18}$F-labelled analogues of EA4 to EA12 may be prepared by analogous $^{18}$F-fluoroalkylation reactions.

Biological Examples

In Vitro Affinity Measurement

Affinity for NR2B receptor was measured using the literature methods of Shoemaker H Allen and Langer S Z (1990), J. Pharmacol. 176, 249-250: NMDA, Polyamine source: Wistar Rat cerebral cortex Ligand: 2Nm [$^3$H]Ifenprodil vehicle: 1% DMSO Incubation time/temperature: 2 hours at 4° C.

Incubation buffer 50Mm Tris-HCl, pH 7.4, 5 µM vanoxerine (GBR-12909, available from Sigma Aldrich) at 25° C.

Non-specific ligand: 10 µM Ifenprodil $K_D$: 0.026 Mm $B_{MAX}$: 1.1 pmole/mg protein* specific binding: 80%*

Quantitation method: radioligand binding significance criteria: ≧50% of maximum stimulation or inhibition.

Ki values were obtained from six different concentrations tested in duplicate. Compounds EA4 to EA6 and EA8 to EA16 had Ki<11 nM, with EA6, EA9, EA10, and EA14 having Ki <2 nM. Compound EA7 had a Ki >100 nM.

Animal Experiments

Male Wister rats (body weight in range of 206-225 g) were used for the determination of regional brain uptake. During the scanning sequence, the animals were kept under isoflurane anesthesia at room temperature. The test compound in question (volume of 0.5-0.7 ml) was administered via injection into a tail vein by bolus injection. Imaging studies were performed using a Focus 120 microPET unit. Data were corrected for the duration of the image acquisition, dead time, randoms, branching ratio, and physical decay of the radionuclide using hardware and software (ASIPro) provided by the manufacturer (Siemens).

Data were collected in 13 time frames of different duration using an energy window of 350-750 keV, and a coincidence timing window 1 of 6 ns. The list-mode data were sorted into 2-dimensional histograms by Fourier rebinning, and transverse images were reconstructed by filtered backprojection and by ordered-subsets expectation maximization (OSEM) iterative reconstruction.

The regions of interest (ROIs) were set in the brain region of choice (e.g. Thalamus, Hippocampal formation, Temporal Cortex, Frontal Cortex) on the voxels obtained in the transversal (axial) reconstructed summed images in the interval 600-2700 post-injection and used for generation of full-length time-activity-uptake curves, FIG. 1 illustrates the ROI selection on a transversal section, in which Is Frontal Cortex, 2 is Temporal Cortex, 3 is Thalamus, 4 is Hippocampal Formation, and 5 is Cerebellum.

26.9 MBq of compound EA11 was administered with a specific activity of 860 mCi/µmol at the time of injection.

Compound EA10 was administered i) in an amount of 32.3 MBq with a specific activity of 1020 mCi/µmol and ii) in a radioactivity amount of 31.3 MBq added authentic reference compound corresponding to 1 mg/kg body weight.

Figure 2:
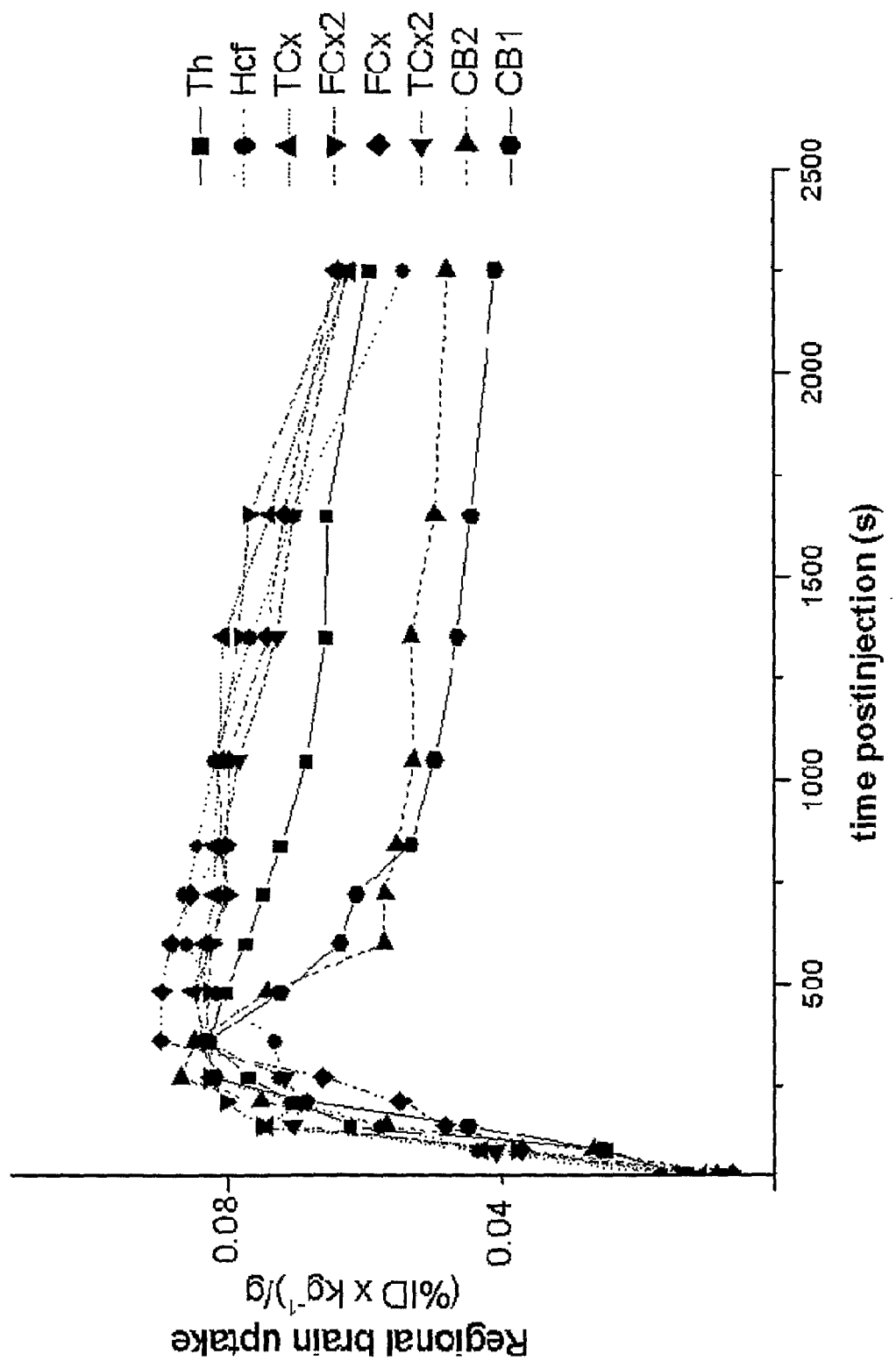
FIG. 2 shows the time activity curves for Compound EA10 in which the following abbreviations are used: Fcx: Frontal cortex; Tcx: Temporal cortex; Th: Thalamus; HcF: Hippocampal Formation; Cb: Cerebellum.
Figure 3:
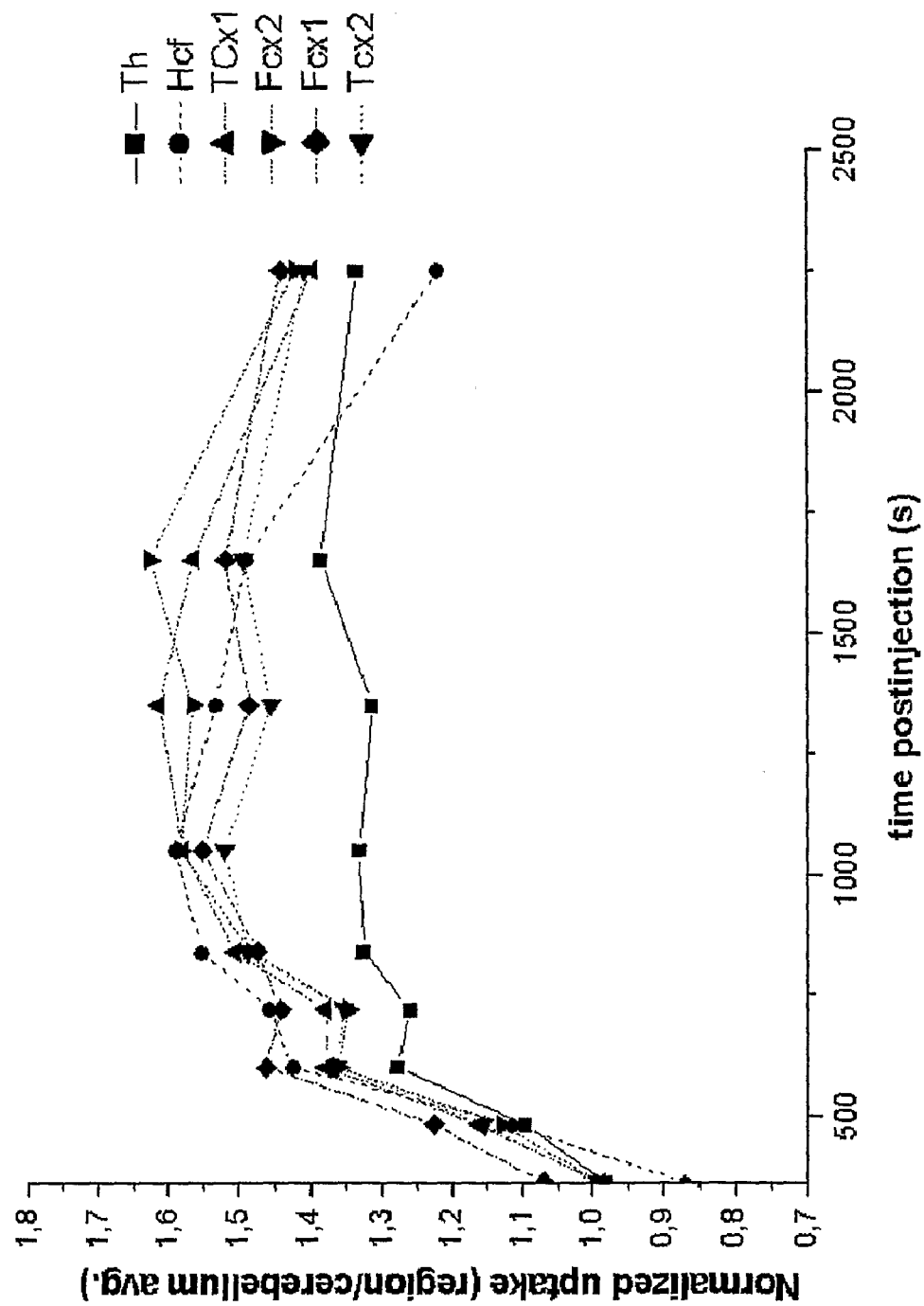
FIGS. 3 and 4 show the region/cerebellum uptake ratios of Compound EA10, no carrier added and carrier added respectively, in which the following abbreviations are used: Fcx: Frontal cortex; Tcx: Temporal cortex; Th: Thalamus; HcF: Hippocampal Formation; Cb: Cerebellum.
Figure 4:
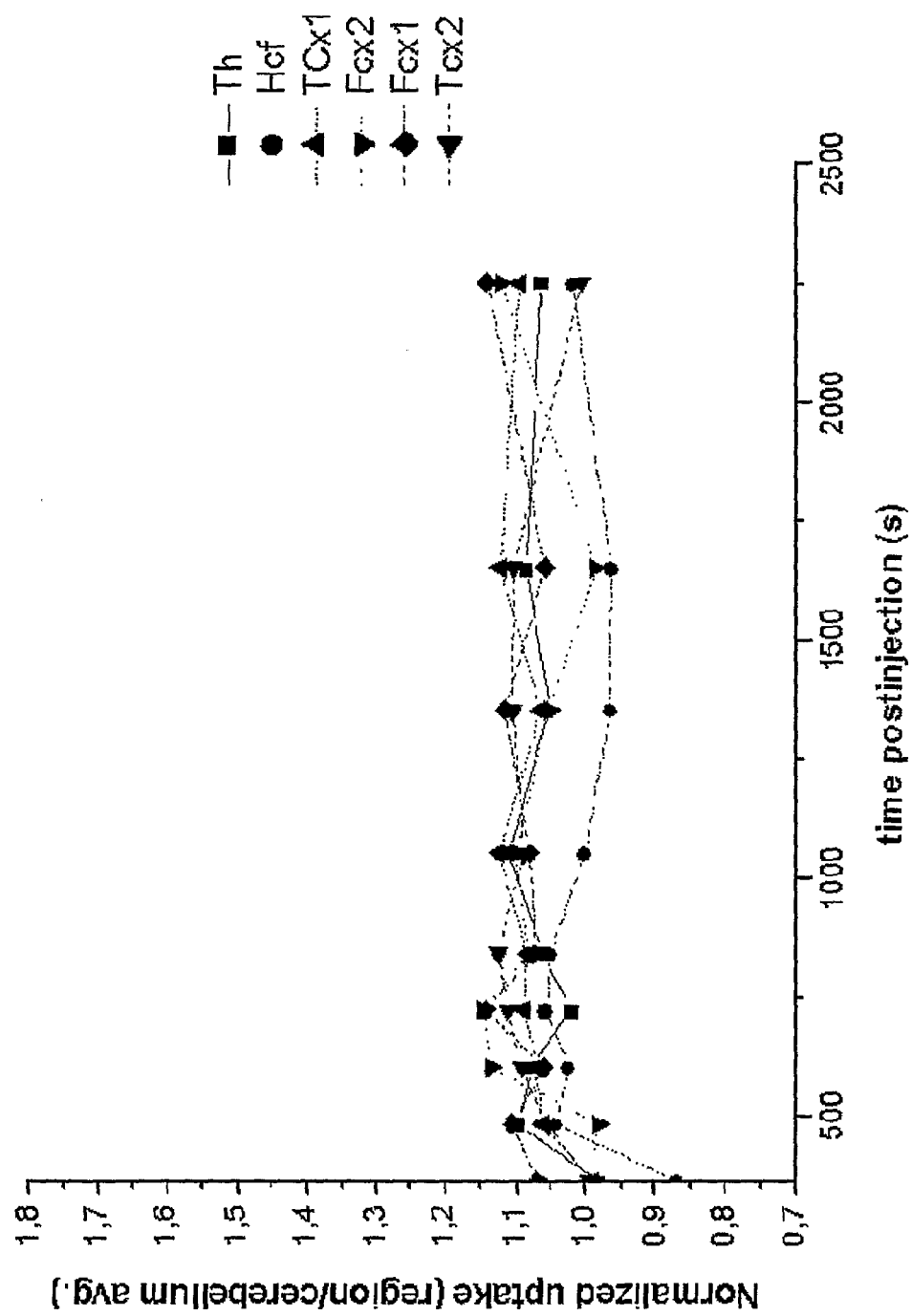

The Results EA10 are shown in FIGS. 2 to 4 in which the following abbreviations are used: Fcx: Frontal cortex; Tcx: Temporal cortex; Th: Thalamus; HcF: Hippocampal Formation; Cb: Cerebellum. FIG. 2 shows the time activity curves for Compound EA10, FIGS. 3 and 4 show the region/cerebellum uptake ratios of Compound EA10, no carrier added and carrier added respectively.

What is claimed is:

1. A compound of formula (Ia)

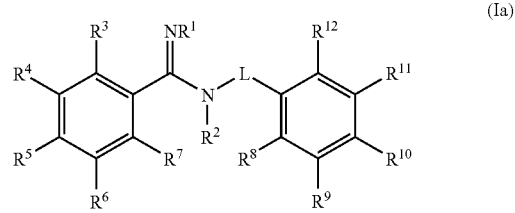

or a salt thereof, wherein
$R^1$ is selected from hydrogen, $C_{1-6}$alkyl, $C_{2-6}$alkenyl, $C_{2-6}$alkynyl, $C_{5-12}$aryl, and $C_{5-12}$hetaryl;

$R^2$ is selected from hydrogen, $C_{1-6}$alkyl, $C_{2-6}$alkenyl, $C_{2-6}$alkynyl, $C_{5-12}$aryl, and $C_{5-12}$hetaryl;

L is $C_{1-6}$alkylene;

one or two of the groups $R^3$ to $R^7$ are independently selected from halo, $C_{1-6}$alkyl, $C_{1-6}$haloalkyl, $C_{1-6}$alkoxy, $C_{1-6}$haloalkoxy and the remaining groups $R^3$ to $R^7$ are hydrogen;

two, three, or four of the groups $R^8$ to $R^{12}$ are independently selected from halo, $C_{1-6}$alkyl, $C_{1-6}$haloalkyl, $C_{1-6}$alkoxy, $C_{1-6}$haloalkoxy and the remaining groups $R^8$ to $R^{12}$ are hydrogen and at least one of the groups $R^8$ to $R^{12}$ comprises a radiolabel selected from $^{11}C$, $^{18}F$, $^{123}I$, $^{124}I$, and $^{122}I$.

2. A compound according to claim 1 wherein $R^5$ is selected from halo, $C_{1-6}$alkyl, $C_{1-6}$haloalkyl, $C_{1-6}$alkoxy, and $C_{1-6}$haloalkoxy and the remaining groups $R^3$ to $R^7$ are hydrogen.

3. A compound according to claim 1 wherein $R^5$ is halo.

4. A compound according to claim 1 which is selected from:

N-(3,5-dimethoxybenzyl)-4-trifluoromethoxyphenyl amidine;
N-(2,5-dimethoxybenzyl)-4-trifluoromethoxyphenyl amidine;
N-(2,6-dimethoxybenzyl)-4-trifluoromethoxyphenyl amidine;
N-(2,3-dimethoxybenzyl)-4-trifluoromethoxyphenyl amidine;
N-(2,5-dimethoxy-4-chlorobenzyl)-4-trifluoromethoxyphenyl amidine;
N-(2-methoxy-5-chlorobenzyl)-4-trifluoromethoxyphenyl amidine;
N-(2-methoxy-5-bromobenzyl)-4-trifluoromethoxyphenyl amidine;
N-(3-methoxy-5-chlorobenzyl)-4-trifluoromethoxyphenyl amidine;
N-(2-methoxybenzyl)-4-iodophenyl amidine;
N-(3-chlorobenzyl)-4-iodophenyl amidine;
N-(3,5-dichlorobenzyl)-4-iodophenyl amidine;
N-(3-(2-fluoroethoxy)-5-chlorobenzyl)-4-trifluoromethoxyphenyl amidine;
N-(3-(2-fluoroethoxy)-5-bromobenzyl)-4-trifluoromethoxyphenyl amidine; and
N-(2-(2-fluoroethoxy)-5-chlorobenzyl)-4-trifluoromethoxyphenyl amidine.

5. A method for in vivo imaging of NMDA receptor in a mammal, which comprises administration of an effective amount of a radiolabelled compound of formula (Ia) as defined in claim 1 or a salt thereof and detecting the uptake of said compound.

6. A method according to claim 5 for diagnosis of a disease in which the NMDA receptor is indicated.

7. A method according to claim 6 wherein the disease is selected from pain, epilepsy, stroke, cerebral ischemia, muscular spasms, Alzheimer's disease, Huntington's disease, Parkinson's disease, schizophrenia, addiction, anxiety, depression, learning disorders, neurotoxicity associated with hypoxia and ischemia, and diabetes.

8. A radiopharmaceutical formulation comprising a compound of formula (Ia) as defined in claim 1 or a salt thereof and at least one pharmaceutically acceptable carrier or excipient, in a form suitable for administration to a mammal.

9. A compound according to claim 3, wherein $R^5$ is $^{123}I$, $^{124}I$ or $^{122}I$.

* * * * *